United States Patent
Memoli et al.

(10) Patent No.: US 12,324,850 B2
(45) Date of Patent: Jun. 10, 2025

(54) COMPOSITIONS AND METHODS FOR CLEANING, DECONTAMINATION AND TREATING SUBJECTS EXPOSED TO CHEMICAL IRRITANTS

(71) Applicant: Reflex Red Storm, LLC., Missoula, MT (US)

(72) Inventors: Patrick Memoli, Missoula, MT (US); Troy Graham, Missoula, MT (US)

(73) Assignee: REFLEX RED STORM, LLC., Missoula, MT (US)

( * ) Notice: Subject to any disclaimer, the term of this patent is extended or adjusted under 35 U.S.C. 154(b) by 955 days.

(21) Appl. No.: 17/299,438

(22) PCT Filed: Dec. 5, 2019

(86) PCT No.: PCT/US2019/064682
§ 371 (c)(1),
(2) Date: Jun. 3, 2021

(87) PCT Pub. No.: WO2020/118055
PCT Pub. Date: Jun. 11, 2020

(65) Prior Publication Data
US 2022/0079859 A1    Mar. 17, 2022

Related U.S. Application Data

(60) Provisional application No. 62/775,959, filed on Dec. 6, 2018.

(51) Int. Cl.
| | |
|---|---|
| A61K 8/44 | (2006.01) |
| A61K 8/20 | (2006.01) |
| A61K 8/41 | (2006.01) |
| A61K 8/60 | (2006.01) |
| A61K 8/92 | (2006.01) |
| A61Q 19/10 | (2006.01) |

(52) U.S. Cl.
CPC .............. *A61K 8/44* (2013.01); *A61K 8/20* (2013.01); *A61K 8/416* (2013.01); *A61K 8/60* (2013.01); *A61K 8/922* (2013.01); *A61Q 19/10* (2013.01)

(58) Field of Classification Search
CPC . A61K 8/44; A61K 8/416; A61K 8/60; A61Q 19/10
See application file for complete search history.

(56) References Cited

U.S. PATENT DOCUMENTS

2010/0086626 A1   4/2010 Reilly

FOREIGN PATENT DOCUMENTS

DE    3403810 A1 *  8/1985

OTHER PUBLICATIONS

Barry et al., "A Randomized Controlled Trial Comparing Treatment Regimens for Acute Pain for Topical Oleoresin Capsaicin (Pepper Spray) Exposure in Adult Volunteers", 2008, Prehospital Emergency Care, 12, Abstract (Year: 2008).*
Winslow et al., "Determination of Optimal Methods of Decontamination After Tear Gas and Pepper Spray Exposure", 2006, Annals of Emergency Medicine, 48, S51 (Year: 2006).*
Malhotra et al., "Chemistry and Toxicity of Tear Gases", 1987, Def Sci J, 37, pp. 281-296 (Year: 1987).*
Smutzer G, Devassy RK. Integrating TRPV1 Receptor Function with Capsaicin Psychophysics. Adv Pharmacol Sci. 2016; 2016:1512457. doi: 10.1155/2016/1512457. Epub Jan. 14, 2016.
European Patent Office, Art 94(3) EPC communication for EP patent application No. 19828124.8 mailed Feb. 8, 2024.
International Search Report and Written Opinion for PCT/US2019/064682. Mailed Mar. 9, 2020. 34 pages.

* cited by examiner

*Primary Examiner* — Brenda L Coleman
*Assistant Examiner* — Madeline E Braun
(74) *Attorney, Agent, or Firm* — Lisa Mueller; Casimir Jones SC

(57) ABSTRACT

The present disclosure is directed to methods of cleansing, decontaminating and/or treating an affected area (such as the mouth, skin, hair, fur, nose, one or both eyes or combinations thereof) of a subject that has been exposed to a chemical irritant such as a cyanocarbon, a capsaicin, an oleoresin *Capsicum* or a vanilloid which binds to a TRPV1 receptor by applying to the affected area (e.g., mouth, skin, hair fur, nose, one or both eyes or combinations thereof), a cleansing, decontaminating and/or effective amount of a composition that comprises at least one salt, at least one zwitterionic surfactant, at least one quaternary ammonium compound, at least one reducing agent and water to decontaminate the affected area.

28 Claims, No Drawings

COMPOSITIONS AND METHODS FOR CLEANING, DECONTAMINATION AND TREATING SUBJECTS EXPOSED TO CHEMICAL IRRITANTS

RELATED APPLICATION INFORMATION

This application claims priority to U.S. Application No. 62/775,959, filed on Dec. 6, 2018, the contents of which are herein incorporated by reference.

FIELD OF THE DISCLOSURE

The present disclosure is directed to compositions for use in methods of cleaning, decontaminating and/or treating an affected area (e.g., mouth, skin, hair, fur, nose, one or both eyes or any combinations thereof) of a subject that has been exposed to one or more chemical irritants such as a cyanocarbon, a capsaicin, an oleoresin *Capsicum*, or a vanilloid which binds to a transient receptor potential vanilloid type 1 (TRPV1) receptor. The compositions described herein comprise at least one salt, at least one zwitterionic surfactant, at least one quaternary ammonium compound, at least one reducing agent and water and are effective in decontaminating or treating an affected area of a subject exposed to one or more such chemical irritants.

BACKGROUND

While exposure to chemical irritants such as cyanocarbons (such as tear gas), capsaicin, oleoresin *capsicums* (pepper spray) and vanilloids which binds to a transient receptor potential vanilloid type 1 (TRPV1) receptor, are generally non-lethal, these irritants cause burning and tearing of the eyes and burning of the skin, hair, fur, nose, mouth and throat, all of which leads to coughing, nasal discharge, disorientation and problems breathing. For those exposed, it is important to provide relief from such irritants as quickly and as conveniently as possible. Therefore, it would be advantageous to have compositions capable of cleansing and/or decontaminating subjects that have been exposed to chemical irritants quickly. More particularly, it would also be beneficial to be able to treat, mitigate, or prevent the undesirable physiological effects associated with chemical irritant exposure.

SUMMARY OF THE DISCLOSURE

In one embodiment, the present disclosure relates to a method for decontaminating skin, hair, fur, one or both eyes or any combination thereof exposed to a cyanocarbon, a capsaicin or derivative thereof. The method comprises the steps of:
  a. providing a subject having exposure or having been exposed to a cyanocarbon, a capsaicin, an oleoresin *Capsicum*, or a vanilloid which binds to a transient receptor potential vanilloid type 1 (TRPV1) receptor; and
  b. decontaminating the skin, hair, fur, one or both eyes, or any combination thereof of the subject with a composition comprising: from about 0.5% to about 1.5 wt % of at least one salt, at least 1.0% to about 3.0 wt % of at least one zwitterionic surfactant, at least about 0.5% to about 1.5 wt % of at least one quaternary ammonium compound, at least about 1% to about 2.5 wt % of at least one reducing agent (such as a reducing sugar) and from about 92.0% to about 97.0% water.

In one aspect of the above method, the subject is exposed to a cyanocarbon. For example, in another aspect, the cyanocarbon is 2-chlorobenzylidene malononitrile.

In yet another aspect of the above method, the subject is exposed or has been exposed to capsaicin, oleoresin *Capsicum* or a vanilloid which binds to a TRPV1 receptor. In yet another aspect, the subject is exposed to capsaicin. In still yet another aspect, the subject is exposed to a vanilloid which binds to a TRPV1 receptor. For example, in one aspect, the vanilloid is omega-hydroxycapsaicin, a dihydrocapsaicin (e.g., 6",7"-dihydro-5',5'"-dicapsaicin), nonivamide, resiniferatoxin, olvanil, and combinations thereof.

In the above method in one aspect, the composition can further comprise from about 0.01 to about 0.5 wt % of at least one fragrance. Examples of fragrances that can be used include citrus oil, orange oil, lemon oil, or combinations thereof. Alternatively, other fragrances which are not citrus oil, orange oil, lemon oil or combinations thereof can also be used (e.g., such as lavender oil, pomegranate oil, bergamot oil, combinations thereof, etc.).

In the above method in one aspect, the water is deionized water.

In the above method in one aspect, the at least one salt is sodium chloride, calcium chloride, potassium chloride, or combinations thereof. In yet another aspect, the salt is sodium chloride.

In the above method in one aspect, the at least one zwitterionic surfactant is a betaine. For example, the betaine can be cocamidopropyl betaine, glycine betaine, a mesomeric betaine or combinations thereof. In another aspect, the betaine is cocamidopropyl betaine.

In the above method in one aspect, the quaternary ammonium compound is benzalkonium chloride, dimethylbenzyl ammonium chloride, stearalkonium chloride, and cetylpyridine chloride, or combinations thereof. In yet another aspect, the quaternary ammonium compound is benzalkonium chloride.

In the above method in one aspect, the reducing agent (e.g., reducing sugar) is sucrose, glucose, fructose, or combinations thereof. In yet another aspect, the reducing agent (or reducing sugar) is sucrose.

In the above method in one aspect, one or both eyes are decontaminated. Alternatively, in another aspect, the skin is decontaminated, optionally, together with one or both eyes. Alternatively, in another aspect, hair or fur is decontaminated, optionally, together with the skin and/or one or both eyes.

In the above method in one aspect, the composition comprises at least one salt is sodium chloride, the at least one zwitterionic surfactant is cocamidopropyl betaine, the at least one reducing agent (e.g., reducing sugar) is sucrose and the water is deionized water. Optionally, the composition further comprises at least one fragrance. In another aspect, the composition comprises about 0.90 wt % of sodium chloride, about 2.0 wt % of cocamidopropyl betaine, about 1.0 wt % of benzalkonium chloride, about 2.0 wt % of sucrose, 0.05% of a fragrance (such as an orange oil).

In another embodiment, the present disclosure relates to a method for treating skin, hair, fur, one or both eyes or combinations thereof exposed to a cyanocarbon, a capsaicin, an oleoresin *Capsicum*, or a vanilloid which binds to a TRPV1 receptor. The method comprises the step of:
  a. providing a subject having exposure or having been exposed to a cyanocarbon, a capsaicin, an oleoresin *Capsicum*, or a vanilloid which binds to a TRPV1 receptor; and b. treating the skin, hair, fur, one or both eyes or combinations thereof of the subject with a composition comprising: from about 0.5% to about 1.5 wt % of at least one salt, at least 1.0% to about 3.0 wt % of at least one zwitterionic surfactant, at least about 0.5% to about 1.5 wt % of at least one quaternary ammonium compound, at least about 1% to about 2.5 wt % of at least one reducing agent and from about 92.0% to about 97.0% water.

In one aspect of the above method, the subject is exposed to a cyanocarbon. For example, in another aspect, the cyanocarbon is 2-chlorobenzylidene malononitrile.

In yet another aspect of the above method, the subject is exposed or has been exposed to capsaicin, oleoresin *Capsicum* or a vanilloid which binds to a TRPV1 receptor. In yet another aspect, the subject is exposed to capsaicin. In yet another aspect, the subject is exposed to a vanilloid which binds to a TRPV1 receptor. For example, in one aspect, the vanilloid is omega-hydroxycapsaicin, a dihydrocapsaicin (e.g., 6",7"-dihydro-5',5'"-dicapsaicin), nonivamide, resiniferatoxin, olvanil, and combinations thereof.

In the above method in one aspect, the composition can further comprise from about 0.01 to about 0.5 wt % of at least one fragrance. Examples of fragrances that can be used include citrus oil, orange oil, lemon oil, or combinations thereof. Alternatively, other fragrances which are not citrus oil, orange oil, lemon oil or combinations thereof can also be used (e.g., such as lavender oil, pomegranate oil, bergamot oil, combinations thereof, etc.).

In the above method in one aspect, the water is deionized water.

In the above method in one aspect, the at least one salt is sodium chloride, calcium chloride, potassium chloride, or combinations thereof. In yet another aspect, the salt is sodium chloride.

In the above method in one aspect, the at least one zwitterionic surfactant is a betaine. For example, the betaine can be cocamidopropyl betaine, glycine betaine, a mesomeric betaine or combinations thereof. In another aspect, the betaine is cocamidopropyl betaine.

In the above method in one aspect, the quaternary ammonium compound is benzalkonium chloride, dimethylbenzyl ammonium chloride, stearalkonium chloride, and cetylpyridine chloride, or combinations thereof. In yet another aspect, the quaternary ammonium compound is benzalkonium chloride.

In the above method in one aspect, the reducing agent (e.g., reducing sugar) is sucrose, glucose, fructose or combinations thereof. In yet another aspect, the reducing agent (or reducing sugar) is sucrose.

In the above method in one aspect, one or both eyes are decontaminated. Alternatively, in another aspect, the skin is decontaminated, optionally, together with one or both eyes. Alternatively, in another aspect, hair or fur is decontaminated, optionally with the skin and/or one or both eyes.

In the above method in one aspect, the composition comprises at least one salt is sodium chloride, the at least one zwitterionic surfactant is cocamidopropyl betaine, the at least one reducing agent (e.g., reducing sugar) is sucrose and the water is deionized water. Optionally, the composition further comprises at least one fragrance. In another aspect, the composition comprises about 0.90 wt % of sodium chloride, about 2.0 wt % of cocamidopropyl betaine, about 1.0 wt % of benzalkonium chloride, about 2.0 wt % of sucrose, 0.05% of a fragrance (such as an orange oil).

DETAILED DESCRIPTION OF THE DISCLOSURE

In one embodiment, the present disclosure relates to compositions, such as cleansing compositions, decontamination compositions, and/or therapeutic or treating compositions as well as the methods of cleansing, decontaminating and/or treating one or more affected areas (such as the mouth, skin, hair, fur, nose, one or both eyes or combinations thereof of a subject (such as a human or animal (e.g. such as a dog, cat, horse, bovine, pig, mouse, rat, etc.) to or from exposure to one or more chemical irritants, such as cyanocarbons, capsaicins, oleoresin *Capsicums*, a vanilloid which binds to a TRPV1 receptor (e.g., omega-hydroxycapsaicin, a dihydrocapsaicin (e.g., 6",7"-dihydro-5',5'"-dicapsaicin), nonivamide, resiniferatoxin, olvanil, and combinations thereof), or any combinations thereof. In one aspect, the compositions described herein can inhibit or minimize the effects of exposure to one or more irritants (such as one or more of cyanocarbons, capsaicins, oleoresin *Capsicums*, a vanilloid which binds to a TRPV1 receptor, or any combinations thereof) by focusing on and interfering with the specific physiological sequences of events that occur in an exposed subject. Similarly, the compositions can cleanse, decontaminate or treat one or more of the mouth, skin, hair, fur, nose and/or one or both eyes or combinations thereof of a subject that has been exposed to other chemical irritant (such as one or more of cyanocarbons, capsaicins, oleoresin *Capsicums*, a vanilloid which binds to a TRPV1 receptor, or any combinations thereof)—containing products such as those used as topical creams, in pepper ball projectiles, and other similar cyanocarbon, capsaicin or capsaicinoid-compositions that contact a subject's mouth, skin, hair, fur, nose, one or both eyes or combinations thereof.

Compositions

The present disclosure relates to compositions that can be used alone, or in combination, to cleanse, decontaminate and/or treat subjects that have been exposed to chemical irritants, specifically, one or more of cyanocarbons, capsaicins, oleoresin *Capsicums*, a vanilloid which binds to a TRPV1 receptor, or any combinations thereof. The compositions can be configured to absorb the chemical irritant from the affected area (such as the mouth, skin, hair, fur, nose, one or both eyes or combinations thereof) so that the amount or concentration of irritant is reduced. Additionally, the compositions can be configured to treat the affected area (e.g., mouth, skin, hair, fur, nose, one or both eyes or combinations thereof) to ameliorate adverse physical responses to the chemical irritant.

The compositions described herein can be used to cleanse, decontaminate and/or treat chemical irritants regardless of their form (namely, whether they are in the form of a solid, liquid or gas (such as aerosol-dispersed irritants)). Specifically, the compositions of the present disclosure are most effective against one or more of cyanocarbons, capsaicins, oleoresin *Capsicums* (pepper spray), or a vanilloid which binds to a TRPV1 receptor. Examples of cyanocarbons include 1-chloroacetophenone (CN); (ii) 2-chlorobenzylidene malononitrile (CS); or (iii) dibenz[b,f]-1,4-oxazepine (CR). Examples of capsaicins include capsaicin (8-methyl-N-vanillyl-trans-6-nonenamide) dihydrocapsaicin (8-methyl-N-vanillylnonaneamide) nordihydrocapsaicin nonivamide (n-vanillynonanamide) homocapsaicin, and homodihydrocapsaicin. Examples of a vanilloid which binds to a TRPV1 receptor include omega-hydroxycapsaicin, a dihydrocapsaicin (e.g., 6",7"-dihydro-5',5'"-dicapsaicin), nonivamide, resiniferatoxin, olvanil, and combinations thereof.

The compositions of the present disclosure contain from about 0.5 wt % to about 1.5 wt % of at least one salt, at least 1.0% wt % to about 3.0 wt % of at least one zwitterionic surfactant, at least about 0.5% wt % to about 1.5 wt % of at least one quaternary ammonium compound, at least about 1% to about 2.5 wt % of at least one reducing agent and from about 85.0 wt % to about 97.0 wt % water.

The at least one salt used in the composition of the present disclosure can be any salt known in the art. In one aspect, the salt is sodium chloride, calcium chloride, potassium chloride, or combinations thereof. In another aspect, the salt is sodium chloride. In one aspect, the salt is present in an amount of about 0.5 wt % to about 1.4 wt %. In yet another aspect, the salt is present in an amount of about 0.5 wt % to about 1.3 wt %. In yet another aspect, the salt is present in an amount of about 0.5 wt % to about 1.2 wt %. In yet another aspect, salt is present in an amount of about 0.5 wt % to about 1.1 wt %. In yet another aspect, the salt is present in an amount of salt is present in an amount of about 0.5 wt % to about 1.0 wt %. In still another aspect, the salt is present in the composition in the amount of about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt % or about 1.5 wt %. In still yet another aspect, the salt is sodium chloride that is present in an amount of about 0.5 wt % to about 1.1 wt %. In yet another aspect, the sodium chloride is present in an amount of about 0.9 wt %.

The at least one zwitterionic surfactant used in the composition of the present disclosure can be any zwitterionic surfactant known in the art. In one aspect, the at least one zwitterionic surfactant that can be used is betaine. Any betaine known in the art can be used, including for example, cocamidopropyl betaine, glycine betaine, a mesomeric betaine or combinations thereof. In one aspect, the at least one zwitterionic surfactant is cocamidopropyl betaine. In yet another aspect, the at least one zwitterionic surfactant is present in an amount of about 1.0 wt % to about 2.9 wt %. In yet another aspect, the one zwitterionic surfactant is present in an amount of about 1.25 wt % to about 2.5 wt %. In yet another aspect, one zwitterionic surfactant is present in an amount of about 1.5 wt % to about 2.25 wt %. In yet another aspect, the one zwitterionic surfactant is present in an amount of salt is present in an amount of about 1.5 wt % to about 2.1 wt %. In still another aspect, the one zwitterionic surfactant is present in the composition in the amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt % about 3.0 wt %. In still yet another aspect, the at least one zwitterionic surfactant is sodium cocamidopropyl betaine that is present in an amount of about 1.5 wt % to about 2.25 wt %. In yet another aspect, at least one zwitterionic surfactant is sodium cocamidopropyl betaine is present in an amount of about 2.0 wt %.

The at least one quaternary ammonium compound used in the composition can be any quaternary ammonium compound known in the art. In one aspect, the at least one quaternary ammonium compound is benzalkonium chloride, dimethylbenzyl ammonium chloride, stearalkonium chloride, and cetylpyridine chloride, or combinations thereof. In yet another aspect, the at least one quaternary ammonium compound is benzalkonium chloride. In another aspect, the at least one quaternary ammonium compound is present in an amount of about 0.5 wt % to about 1.4 wt %. In yet another aspect, the at least one quaternary ammonium compound is present in an amount of about 0.5 wt % to about 1.3 wt %. In yet another aspect, the at least one quaternary ammonium compound is present in an amount of about 0.5 wt % to about 1.2 wt %. In yet another aspect, the at least one quaternary ammonium compound is present in an amount of about 0.5 wt % to about 1.1 wt %. In yet another aspect, the at least one quaternary ammonium compound is present in an amount of salt is present in an amount of about 0.5 wt % to about 1.0 wt %. In still another aspect, the at least one quaternary ammonium compound is present in the composition in the amount of about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt % or about 1.5 wt %. In still yet another aspect, the at least one quaternary ammonium compound is cocamidopropyl betaine that is present in an amount of about 0.5 wt % to about 1.1 wt %. In yet another aspect, the cocamidopropyl betaine is present in an amount of about 1.0 wt %.

The at least one reducing agent that can be used in the composition can be any reducing agent known in the art. Specifically, the reducing agent can be a reducing sugar which reacts via a free aldehyde or ketone group. In one aspect, the reducing agent or reducing sugars are sucrose, glucose, fructose or combinations thereof. In yet another aspect, the at least one reducing agent or reducing sugar is present in an amount of about 1.0 wt % to about 2.4 wt %. In yet another aspect, the one reducing agent or reducing sugar is present in an amount of about 1.25 wt % to about 2.3 wt %. In yet another aspect, one reducing agent or reducing sugar is present in an amount of about 1.5 wt % to about 2.25 wt %. In yet another aspect, the one reducing agent or reducing sugar is present in an amount of salt is present in an amount of about 1.5 wt % to about 2.1 wt %. In still another aspect, the one reducing agent or reducing sugar is present in the composition in the amount of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.1 wt %, about 2.2 wt %, about 2.3 wt %, about 2.4 wt % or about 2.5%. In still yet another aspect, the at least one reducing agent or reducing sugar is sucrose that is present in an amount of about 1.5 wt % to about 2.1 wt %. In yet another aspect, the least one reducing agent or reducing sugar is sucrose is present in an amount of about 2.0 wt %.

The composition also contains water, such as deionized water. Generally, once the above ingredients and any additional ingredients (such as a fragrance) is added, the balance or remaining portion of the composition is water. Thus, the amount of water contained in the composition is not critical and can be, for example, between about 85 wt % to 98 wt %. In yet another aspect, the composition contains about 88 wt % to about 98 wt % of water. In yet a further aspect, the composition contains about 92% wt % to about 97 wt % of water. In one aspect, the composition contains about 85 wt % of water. In another aspect, the composition contains about 86 wt % of water. In one aspect, the composition contains about 87 wt % of water. In one aspect, the composition contains about 88 wt % of water. In one aspect, the composition contains about 89 wt % of water. In one aspect, the composition contains about 90 wt % of water. In one aspect, the composition contains about 91 wt % of water. In one aspect, the composition contains about 92 wt % of water. In one aspect, the composition contains about 93 wt % of water. In one aspect, the composition contains about 94 wt % of water. In one aspect, the composition contains about 95 wt % of water. In one aspect, the composition contains about 96 wt % of water. In one aspect, the composition contains about 97 wt % of water. In one aspect, the composition contains about 98 wt % of water. In yet another aspect, the composition contains deionized water in an amount of about 92 wt %. In yet another aspect, the composition contains deionized water in an amount of about 93 wt %. In yet another aspect, the composition contains deionized water in an amount of about 93.5 wt %. In yet another aspect, the composition contains deionized water in an amount of about 94 wt %.

In addition to the above ingredients, the composition can also contain one or more additional ingredients. For example, in one aspect, the composition contains a fragrance. In one aspect, the fragrance is a citrus oil, such as an orange oil, lemon oil, lime oil, etc. In another aspect, the fragrance is present in an amount of about 0.01 wt % to about 0.5 wt %. In yet another aspect, the fragrance is present in an amount of about 0.05 wt % to about 0.5 wt %. In yet another aspect, the fragrance is present in an amount of about 0.05 wt % to about 0.1 wt %. In one aspect, the fragrance is present in an amount of about 0.01 wt %. In yet another aspect, the fragrance is present in an amount of about 0.05 wt %. In yet another aspect, the fragrance is present in an amount of about 0.1 wt %. In yet another aspect, the fragrance is present in an amount of about 0.5 wt %. In yet another aspect, the fragrance is orange oil. In yet still another aspect, the fragrance is orange oil that is present in the composition in an amount of 0.05% wt %. In addition, the composition can also contain one or more pH modifiers or additional or alternative fragrances to citrus oils (such as lavender oil, pomegranate oil, etc.)

Example compositions of the present disclosure include:
a. about 0.90 wt % of sodium chloride, about 2.0 wt % of cocamidopropyl betaine, about 1.0 wt % of benzalkonium chloride, about 2.0 wt % of sucrose, 0.05 wt % of a fragrance.
b. about 0.90 wt % of potassium chloride, about 2.0 wt % of cocamidopropyl betaine, about 1.0 wt % of benzalkonium chloride, about 2.0 wt % of sucrose, 0.05 wt % of a fragrance.
c. about 0.90 wt % of sodium chloride, about 2.0 wt % of glycine betaine, about 1.0 wt % of benzalkonium chloride, about 2.0 wt % of sucrose, 0.05 wt % of a fragrance.
d. about 0.90 wt % of sodium chloride, about 2.0 wt % of cocamidopropyl betaine, about 1.0 wt % of stearalkonium chloride, about 2.0 wt % of sucrose, 0.05 wt % of a fragrance.
e. about 0.90 wt % of sodium chloride, about 2.0 wt % of cocamidopropyl betaine, about 1.0 wt % of benzalkonium chloride, about 2.0 wt % of fructose, 0.05 wt % of a fragrance.
f. about 0.90 wt % of calcium chloride, about 2.0 wt % of mesomeric betaine, about 1.0 wt % of benzalkonium chloride, about 2.0 wt % of sucrose, 0.05 wt % of a fragrance.
g. about 0.90 wt % of sodium chloride, about 2.0 wt % of cocamidopropyl betaine, about 1.0 wt % of cetylpyridine chloride, about 2.0 wt % of sucrose, 0.05 wt % of a fragrance.
h. about 0.90 wt % of sodium chloride, about 2.0 wt % of cocamidopropyl betaine, about 1.0 wt % of benzalkonium chloride, about 2.0 wt % of glucose, 0.05 wt % of a fragrance.

The compositions described herein are configured such that they are capable of being introduced and delivered to the affected area (e.g., mouth, skin, hair, fur, nose, eyes (one or both) or combinations thereof) of subject so as to interfere or short-circuit the capsaicin receptor-mediated process and/or cascading signaling events that produce acute and/or prolonged pain as well as any inflammation resulting from the exposure to the chemical irritant. However, it should be recognized that complete prevention of pain perception may not occur since these processes are immediate and are initiated by initial exposure to the chemical irritant. As such, the compositions of the present disclosure are configured to minimize these physiological sensations faster than natural physiological mechanisms for clearance, which can last up to about 24 through 48 hours after exposure. Thus, the compositions can be used for removing and/or inactivating the irritant, decreasing the magnitude of the pain sensation, providing general irritant decontamination, and/or treating or preventing physiological effects that arise from exposure to the irritant.

The compositions of the present disclosure (whether used as a cleansing, decontamination and/or therapeutic composition) can be formulated into a delivery system and packaging for convenience and easy use. As such, the compositions can be prepared as liquids, gels, pastes, creams, and the like. Also, the compositions can be absorbed into absorbent matrices such as wipes, which can be used for the application of the compositions as described herein. Alternatively, liquids, gels, pastes, creams, or wipes impregnated with the compositions described herein can be supplied in rigid containers or soft packages. Each container or pouch can hold multiple towels and have easy access. Additionally, the compositions can be included into a container such as a gel tub, pump spray container, and a stick-applicator container. In addition to the aforementioned types of containers, the compositions can be included in a pump sprayer. When the pump sprayer is used, it can be beneficial for the composition to be free-flowing so as to be capable of being sprayed onto or into the contaminated area. Also, the gel tub can be suitable container for gel, paste, or cream compositions that can be applied by hand or with a wipe. Moreover, a stick-applicator container can include the compositions formulated to be in the form of a stick or gel similar to a common deodorant or lip-balm container.

Methods of Cleaning, Decontaminating or Treating a Subject that has been Exposed to One or More Chemical Irritants The adverse effects on the mouth, skin, hair, fur, nose, one or both eyes or combinations thereof upon exposure and contamination with or to one or more chemical irritants, such as at least one cyanocarbon, capsaicin, oleoresin *Capsicum*, a vanilloid which binds to a TRPV1 receptor, or any combinations thereof, begin to subside (but do not go away) within about 1 to about 2 hours with varying degrees of side effects depending upon the individual and scenario involving exposure. As such, the compositions described herein can be used to reduce the duration of such adverse effects as well as inhibit the onset of such adverse effects. Thus, the compositions of the present disclosure can be used to treat or prevent persistent minor coughing, airway irritation, congestion, enhanced thermal sensitivity, and/or hyperalgesia at exposed skin, hair, fur, mouth and nose sites, ocular discomfort (e.g. one or both eyes) and continued accidental re-exposure.

Some chemical irritants can be absorbed through the dermis. As such, such dermal absorption can result in the irritant being sequestered in lipids and proteins. The irritant can then diffuse from the lipids and proteins and produce adverse physiological actions. Additionally, a portion of the absorbed irritant can be metabolized. During the absorption phase, it can be advantageous to apply the compositions of the present disclosure to the skin. This can allow for composition to absorb free irritants to inhibit further physiological activity. Also, such absorption can decrease the effective concentration of the irritant at the skin and increase diffusion of the sequestered capsaicin from the lipids and proteins.

After dermal absorption and sequestration, the irritant can then be distributed throughout the surrounding tissue and body. In some instances, the irritant is systemically absorbed where it can be metabolized. Alternatively, the irritant can be absorbed into tissues retaining sensory nerves, and can result in sensory nerve activation. The activation of the sensory nerves can then cause release of inflammatory mediators and thereby stimulate adjacent cells. This can lead to the subject exposed to the irritant to experience the action potential of pain and heat. During the activation phase, it can be advantageous to apply the composition to the mouth, nose, skin, hair, fur, one or both eyes, or combinations thereof. This can allow for the compositions described herein to counteract the adverse effects of the irritant and inhibit receptor activation. Thus, the compositions can inhibit further physiological activity.

In one embodiment, the compositions of the present disclosure can be used to clean and/or decontaminate the affected area (such as the mouth, nose, skin, hair, fur, or eyes) to effectively remove as much of chemical irritant from that area as possible. As such, applying the composition to the contaminated area can be referred to as the cleansing phase. In one aspect, the composition is applied to the affected area in an amount that decreases the amount of the chemical irritant on that area (such as on the skin, hair, fur, nose, mouth, one or both eyes or combinations thereof). This cleansing phase can include a single or repeated (e.g., 2 times, 3 times, 4 times, 5 times, 6 times, 7 times, etc.) application of generous amounts of the cleansing composition to the affected area. Blotting and/or wiping the affected area clean so as to remove the composition and absorbed chemical irritants from the affected area can follow each application of the composition. For example, when the composition is used as a cleansing composition, it can be applied and removed by being impregnated within a wipe that can be wiped over the contaminated area (such as, for example, the skin, hair, fur, one or both eyes, or combinations thereof etc.). Alternatively, the cleaning composition can be applied as a liquid in a pump sprayer.

In another embodiment, the cleansing and decontamination of an area exposed to an irritant can be performed with the additional use of water. Such a method of cleansing and decontamination of the affected area can include the following: application of a sufficient amount of a cleansing composition to the affected area; washing the affected area vigorously immediately with the cleansing composition to produce a lather; rinsing with cold water to remove the lather; repeating the application, washing, and rinsing steps from 2 to 7 times within a few minutes and repeating as needed if discomfort persists.

In another embodiment, the cleansing and decontamination of an affected area exposed to a chemical irritant can be performed without water. Such a method of cleansing and decontamination of an affected area can include the following: apply a sufficient amount of a cleansing composition to the affected area; washing the affected area vigorously immediately with the cleansing composition to produce a lather; wipe the lather from the skin with a cloth, towel, or the like; repeat the application, wash, and wipe steps, such as from 2 to 7 times within a few minutes; repeat if discomfort persists.

In another embodiment, the composition can be used to effectively inhibit a physiological response from exposure of the affected area to the chemical irritant. The compositions of the present disclosure can be applied to an affected area (mouth, skin, hair, fur, nose, one or both eyes or combinations thereof), after it has been cleansed. As such, applying the composition described herein to cleansed skin can be referred to as the treating or decontaminating phase. In any event, when the composition of the present disclosure as used to treat the subject, the composition can be applied to the affected area in an amount that inhibits the physiological response to the chemical irritant and sooths the affected area. The treating or decontamination phase can include a single or repeated (e.g., 2 times, 3 times, 4 times, 5 times, 6 times, 7 times, etc.) application of generous amounts of the composition to the skin. The composition can be left on the skin for an extended duration and reapplied as needed.

In yet another embodiment, the cleansing, decontamination, and/or therapeutic compositions can be used to decontaminate exposure to one or more chemical irritants. More particularly, the compositions can be used to treat or prevent a variety of physiological effects resulting from exposure to chemical irritants, such as severe dermal irritation that is characterized by an intense burning and itching sensation, erythema, reddening of the skin, and localized tissue inflammation due to plasma extravasations. Also, decontamination and treatment of the affected area, particularly the skin, will tend to mitigate the uncontrollable coughing, shortness of breath, disorientation, confusion, and temporary blindness associated with exposure to the chemical irritant. Moreover, the compositions can treat or prevent other major symptoms of chemical irritant exposure including uncontrollable coughing (capsaicin, for example, is a prototypical inducer of the cough reflex), shortness of breath, disorientation, confusion, and temporary blindness.

The above described uses of the cleansing, decontaminating, and/or therapeutic compositions can include applying the compositions to an affected area, and removing the composition after the desired effect has been obtained. More particularly, a method for cleansing, treating, and/or decontaminating skin that has been exposed to a chemical irritant can include acts of: applying a composition, as a cleaning composition, to the affected area (e.g., mouth, skin, hair, fur, eye or nose) in an amount sufficient to absorb the irritant into the cleansing composition; removing the cleansing composition from the affected area; and applying the composition to the affected area as a therapeutic composition in an amount sufficient to inhibit or treat a physiological effect associated with exposure to the one or more chemical irritants.

In one aspect, the methods of using the compositions can include applying the decontamination composition to the contaminated area (e.g., skin, hair, fur, nose, mouth, one or both eyes or combinations thereof), and then removing the decontamination composition. Additionally, this act can be repeated until the desired effect is achieved or until the chemical irritants been removed from the affected area. Optionally, the therapeutic composition can be administered to the affected area after the decontamination composition has been removed. Thus, the decontamination composition can be substituted for the cleansing and/or therapeutic composition.

An example of a use for the compositions of the present disclosure are as products that address the skin irritation due to exposure of law enforcement chemical agents such as OC. The primary benefit of the present disclosure will be to reduce skin and eye irritation faster than the traditional wash, air, and time. Additionally, the compositions of the present disclosure are useful for officers who need to have their skin and stop eyes from burning as immediately as possible so these individuals can get back to training or work.

It will be readily apparent to those skilled in the art that other suitable modifications and adaptations of the methods of the present disclosure described herein are readily applicable and appreciable and may be made using suitable equivalents without departing from the scope of the present disclosure or the aspects and embodiments disclosed herein. Having now described the present disclosure in detail, the same will be more clearly understood by reference to the following example, which is merely intended only to illustrate some aspects and embodiments of the disclosure and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Preparation of Decontaminate

An aqueous decontaminate composition is prepared in accordance with embodiments of the present disclosure, which includes the following ingredients in approximate amounts: 0.9 wt % sodium chloride; 2.0 wt % potassium metabisulfite; 3.0 wt % cocamidopropyl betaine (CAPB); 1.0 wt % benzalkonium chloride; 0.05 wt % orange oil; and the balance being water.

Example 2

Preparation of Decontaminate

An aqueous decontaminate composition is prepared in accordance with embodiments of the present disclosure, which includes the following ingredients in approximate amounts: 0.9 wt % sodium chloride; 2.0 wt % sucrose; 1.5 wt % cocamidopropyl betaine (CAPB); 0.5 wt % benzalkonium chloride; 0.05 wt % orange oil; and the balance being water.

Example 3

Preparation of Decontaminate

An aqueous decontaminate composition is prepared in accordance with embodiments of the present disclosure, which includes the following ingredients in approximate amounts: 0.9 wt % sodium chloride; 0.5 wt % sodium glucarate; 3.0 wt % cocamidopropyl betaine (CAPB); 1.0% benzalkonium chloride; 0.05 wt % orange oil; and the balance being water.

Example 4

Preparation of Decontaminate

An aqueous decontaminate composition is prepared in accordance with embodiments of the present disclosure, which includes the following ingredients in approximate amounts: 0.9 wt % sodium chloride; 1.0 wt % glycerin; 3.0 wt % cocamidopropyl betaine (CAPB); 1.0 wt % benzalkonium chloride; 0.05 wt % orange oil; and the balance being water.

Example 5

Preparation of Decontaminate

An aqueous decontaminate composition is prepared in accordance with embodiments of the present disclosure, which includes the following ingredients in approximate amounts: 0.9 wt % sodium chloride; 0.5 wt % ethyl alcohol; 3.0 wt % cocamidopropyl betaine (CAPB); 1.0% benzalkonium chloride; 0.05 wt % orange oil; and the balance being water.

Example 6

Preparation of Decontaminate

An aqueous decontaminate composition is prepared in accordance with embodiments of the present disclosure, which includes the following ingredients in approximate amounts: 0.9 wt % sodium chloride; 2.0 wt % sucrose; 3.0 wt % cocamidopropyl betaine (CAPB); 1.0 wt % benzalkonium chloride; 0.05 wt % orange oil; and the balance being water.

Example 7

Preparation of Decontaminate

An aqueous decontaminate composition is prepared in accordance with embodiments of the present disclosure, which includes the following ingredients in approximate amounts: 0.9 wt % sodium chloride; 2.0 wt % sucrose; 1.5 wt % cocamidopropyl betaine (CAPB); 0.5% benzalkonium chloride; 0.05% orange oil; and the balance being water.

Example 8

Preparation of Decontaminate

An aqueous decontaminate composition is prepared in accordance with embodiments of the present disclosure, which includes the following ingredients in approximate amounts: 0.9 wt % sodium chloride; 2.0 wt % sucrose; 2.0 wt % cocamidopropyl betaine (CAPB); 1.0 wt % benzalkonium chloride; 0.05 wt % orange oil; and the balance being water.

Example 9

Efficacy Test of Decontaminate on Standardized Fabric Samples Dosed with Reflex Protect CS Gel A test was conducted to determine the efficacy of test decontaminate formulations to remove CS Gel from a number of standardized swatches of variable fabric types. The fabric types were selected as representative of common clothing fabrics and are produced by the Center for Testmaterials B.V. They are as follows; PCN-01, a 65%/35% polyester/cotton blend; CN-42, a Nylon; and CN-11, a 100% cotton.

Each 2 in.×2 in. fabric swatch was dosed with 3 full sprays from a 3.0 oz. finger pump spray bottle. They were let air dry for ~10 minutes. Each of the fabric types was sprayed by each test formulation with 3 full sprays from a 3.0 oz. finger pump spray bottle. The fabric swatches were let air dry for ~10 minutes.

To determine efficacy, each of the fabric swatches was evaluated by a panel of researchers based on olfactory sense of the loss of 'peppery' odor and visual analysis of the loss of 'orange' color of the CS Gel. The swatches were ranked based on the amount of CS Gel the researcher perceived was remaining after application of decontaminates.

It is understood that the foregoing detailed description and accompanying examples are merely illustrative and are not to be taken as limitations upon the scope, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use, may be made without departing from the spirit and scope thereof.

For reasons of completeness, various aspects are set out in the following numbered clauses:

Clause 1. A method for decontaminating skin, hair, fur, one or both eyes or combinations thereof exposed to a cyanocarbon, a capsaicin or derivative thereof, the method comprising the steps of:
  a. providing a subject having exposure to a cyanocarbon, a capsaicin, an oleoresin *Capsicum*, or a vanilloid which binds to a TRPV1 receptor; and
  b. decontaminating the skin, hair, fur, or eyes of the subject with a composition comprising: from about 0.5% to about 1.5 wt % of at least one salt, at least 1.0% to about 3.0 wt % of at least one zwitterionic surfactant, at least about 0.5% to about 1.5 wt % of at least one quaternary ammonium compound, at least about 1% to about 2.5 wt % of at least one reducing agent and from about 92.0% to about 97.0% water.

Clause 2. The method of clause 1, wherein the subject is exposed to a cyanocarbon.

Clause 3. The method of clause 2, wherein the cyanocarbon is 2-chlorobenzalmalononitrile.

Clause 4. The method of clause 1, wherein the subject is exposed to capsaicin, oleoresin *Capsicum* or a vanilloid which binds to a TRPV1 receptor.

Clause 5. The method of clause 4, wherein the subject is exposed to capsaicin.

Clause 6. The method of clause 1, wherein the composition further comprises from about 0.01 to about 0.5 wt % of at least one fragrance.

Clause 7. The method of clause 6, wherein the at least one fragrance is citrus oil, lemon oil, orange oil or combinations thereof.

Clause 8. The method of any of clauses 1-7, wherein the water is deionized water.

Clause 9. The method of any of clauses 1-8, wherein the at least one salt is sodium chloride, calcium chloride, potassium chloride, or combinations thereof.

Clause 10. The method of any of clauses 1-9, wherein the at least one zwitterionic surfactant is a betaine.

Clause 11. The method of clause 10, wherein the betaine is cocamidopropyl betaine, glycine betaine, a mesomeric betaine or combinations thereof.

Clause 12. The method of any one of clauses 1-11, wherein the quaternary ammonium compound is benzalkonium chloride, dimethylbenzyl ammonium chloride, stearalkonium chloride, and cetylpyridine chloride, or combinations thereof.

Clause 13. The method of any one of clauses 1-12, wherein the reducing agent is sucrose, glucose, fructose or combinations thereof.

Clause 14. The method of any one of clauses 1-13, wherein one or both eyes are decontaminated.

Clause 15. The method of any one of clauses 1-14, wherein the skin is decontaminated.

Clause 16. The method of any one of clauses 1-15, wherein the at least one salt is sodium chloride, the at least one zwitterionic surfactant is cocamidopropyl betaine, the at least one reducing agent is sucrose and the water is deionized water.

Clause 17. The method of clause 16, wherein the composition further comprises a fragrance.

Clause 18. The method of clause 17, wherein the composition comprises about 0.90 wt % of sodium chloride, about 2.0 wt % of cocamidopropyl betaine, about 1.0 wt % of benzalkonium chloride, about 2.0 wt % of sucrose, 0.05% of a fragrance.

Clause 19. The method of clause 18, wherein the fragrance is orange oil.

Clause 20. A method for treating skin, hair, fur, one or both eyes or combinations thereof exposed to a cyanocarbon, a capsaicin, an oleoresin *Capsicum* or a vanilloid which binds to a TRPV1 receptor, the method comprising the steps of:
  a. providing a subject having exposure to a cyanocarbon, a capsaicin, an oleoresin *Capsicum*, or a vanilloid which binds to a TRPV1 receptor; and
  b. treating the skin, hair, fur, or eyes of the subject with a composition comprising: from about 0.5% to about 1.5 wt % of at least one salt, at least 1.0% to about 3.0 wt % of at least one zwitterionic surfactant, at least about 0.5% to about 1.5 wt % of at least one quaternary ammonium compound, at least about 1% to about 2.5 wt % of at least one reducing agent and from about 92.0% to about 97.0% water.

Clause 21. The method of clause 20, wherein the subject is exposed to a cyanocarbon.

Clause 22. The method of clause 21, wherein the cyanocarbon is 2-chlorobenzylidene malononitrile.

Clause 23. The method of clause 20, wherein the subject is exposed to capsaicin, oleoresin *Capsicum* or a vanilloid which binds to a TRPV1 receptor.

Clause 24. The method of clause 23, wherein the subject is exposed to capsaicin.

Clause 25. The method of clause 20, wherein the composition further comprises from about 0.01 to about 0.5 wt % of at least one fragrance.

Clause 26. The method of clause 25, wherein the at least one fragrance is citrus oil, orange oil, lemon oil or combinations thereof.

Clause 27. The method of any of clauses 20-26, wherein the water is deionized water.

Clause 28. The method of any of clauses 20-27, wherein the at least one salt is sodium chloride, calcium chloride, potassium chloride, or combinations thereof.

Clause 29. The method of any of clauses 20-28, wherein the at least one zwitterionic surfactant is a betaine.

Clause 30. The method of clause 29, wherein the betaine is cocamidopropyl betaine, glycine betaine, a mesomeric betaine or combinations thereof.

Clause 31. The method of any one of clauses 20-30, wherein the quaternary ammonium compound is benzalkonium chloride, dimethylbenzyl ammonium chloride, stearalkonium chloride, and cetylpyridine chloride, or combinations thereof.

Clause 32. The method of any one of clauses 20-31, wherein the reducing agent is sucrose, glucose, fructose or combinations thereof.

Clause 33. The method of any one of clauses 20-32, wherein one or both eyes are decontaminated.

Clause 34. The method of any one of clauses 20-33, wherein the skin is decontaminated.

Clause 35. The method of any one of clauses 20-34, wherein the at least one salt is sodium chloride, the at least one zwitterionic surfactant is cocamidopropyl betaine, the at least one reducing agent is sucrose and the water is deionized water.

Clause 36. The method of clause 35, wherein the composition further comprises a fragrance.

Clause 37. The method of clause 35, wherein the composition comprises about 0.90 wt % of sodium chloride, about 2.0 wt % of cocamidopropyl betaine, about 1.0 wt % of benzalkonium chloride, about 2.0 wt % of sucrose, 0.05% of a fragrance.

Clause 38. The method of clause 37, wherein the fragrance is orange oil.

Clause 39. The method of any of clauses 1-15 or 20-34, wherein hair is decontaminated.

Clause 40. The method of any of clauses 1-15 or 20-34, wherein fur is decontaminated.

Clause 41. The method of any of claims 1-19 or 39-40, wherein the vanilloid which binds to a TRPV1 receptor is omega-hydroxycapsaicin, a dihydrocapsaicin, nonivamide, resiniferatoxin, olvanil and combinations thereof.

Clause 42. The method of any of claims 20-40, wherein the vanilloid which binds to a TRPV1 receptor is omega-hydroxycapsaicin, a dihydrocapsaicin, nonivamide, resiniferatoxin, olvanil and combinations thereof.

What is claimed is:

1. A method for decontaminating skin or eyes exposed to a cyanocarbon, a capsaicin, an oleoresin *capsicum*, or a vanilloid which binds to a TRPV1 receptor, the method comprising the steps of:
    a. providing a subject having exposure to a cyanocarbon, a capsaicin, an oleoresin *capsicum*, or a vanilloid which binds to a TRPV1 receptor; and
    b. decontaminating the skin or eyes of the subject with a composition comprising:
        from about 0.5 wt % to about 1.5 wt % of at least one salt, wherein the at least one salt is sodium chloride, calcium chloride, potassium chloride, or combinations thereof,
        at least 1.0 wt % to about 3.0 wt % of at least one zwitterionic surfactant, wherein the at least one zwitterionic surfactant is cocamidopropyl betaine, glycine betaine, a mesomeric betaine or combinations thereof,
        at least about 0.5 wt % to about 1.5 wt % of at least one quaternary ammonium compound, wherein the quaternary ammonium compound is benzalkonium chloride, dimethylbenzyl ammonium chloride, stearalkonium chloride, and cetylpyridine chloride, or combinations thereof,
        at least about 1 wt % to about 2.5 wt % of at least one reducing agent, wherein the reducing agent is sucrose, glucose, fructose or combinations thereof, and
        from about 92 wt % to about 97.0 wt % water.

2. The method of claim 1, wherein the subject is exposed to a cyanocarbon.

3. The method of claim 2, wherein the cyanocarbon is 2-chlorobenzylidene malononitrile.

4. The method of claim 1, wherein the subject is exposed to capsaicin, oleoresin *capsicum* or a vanilloid which binds to a TRPV1 receptor.

5. The method of claim 4, wherein the subject is exposed to capsaicin.

6. The method of claim 1, wherein the composition further comprises from about 0.01 wt % to about 0.5 wt % of at least one fragrance.

7. The method of claim 6, wherein the at least one fragrance is citrus oil, orange oil, lemon oil, or combinations thereof.

8. The method of claim 1, wherein the water is deionized water.

9. The method of claim 1, wherein one or both eyes are decontaminated.

10. The method of claim 1, wherein the skin is decontaminated.

11. The method of claim 1, wherein the at least one salt is sodium chloride, the at least one zwitterionic surfactant is cocamidopropyl betaine, the at least one reducing agent is sucrose and the water is deionized water.

12. The method of claim 11, wherein the composition further comprises a fragrance.

13. The method of claim 12, wherein the composition comprises about 0.90 wt % of sodium chloride, about 2.0 wt % of cocamidopropyl betaine, about 1.0 wt % of benzalkonium chloride, about 2.0 wt % of sucrose, 0.05 wt % of a fragrance.

14. The method of claim 13, wherein the fragrance is orange oil.

15. A method for treating skin or eyes exposed to a cyanocarbon, a capsaicin, an oleoresin *capsicum*, or a vanilloid which binds to a TRPV1 receptor, the method comprising the steps of:
    a. providing a subject having exposure to a cyanocarbon, a capsaicin, an oleoresin *capsicum*, or a vanilloid which binds to a TRPV1 receptor; and
    b. treating the skin or eyes of the subject with a composition comprising:
        from about 0.5 wt % to about 1.5 wt % of at least one salt, wherein the at least one salt is sodium chloride, calcium chloride, potassium chloride, or combinations thereof,
        at least 1.0 wt % to about 3.0 wt % of at least one zwitterionic surfactant, wherein the at least one zwitterionic surfactant is cocamidopropyl betaine, glycine betaine, a mesomeric betaine or combinations thereof,
        at least about 0.5 wt % to about 1.5 wt % of at least one quaternary ammonium compound, wherein the quaternary ammonium compound is benzalkonium chloride, dimethylbenzyl ammonium chloride, stearalkonium chloride, and cetylpyridine chloride, or combinations thereof,
        at least about 1 wt % to about 2.5 wt % of at least one reducing agent, wherein the reducing agent is sucrose, glucose, fructose or combinations thereof, and
        from about 92 wt % to about 97.0 wt % water.

16. The method of claim 15, wherein the subject is exposed to a cyanocarbon.

17. The method of claim 16, wherein the cyanocarbon is 2-chlorobenzylidene malononitrile.

18. The method of claim 15, wherein the subject is exposed to capsaicin, oleoresin *capsicum* or a vanilloid which binds to a TRPV1 receptor.

19. The method of claim 18, wherein the subject is exposed to capsaicin.

20. The method of claim 15, wherein the composition further comprises from about 0.01 wt % to about 0.5 wt % of at least one fragrance.

21. The method of claim 20, wherein the at least one fragrance is citrus oil, orange oil, lemon oil, or combinations thereof.

22. The method of claim 15, wherein the water is deionized water.

23. The method of claim 15, wherein one or both eyes are treated.

24. The method of claim 15, wherein the skin is treated.

25. The method of claim 15, wherein the at least one salt is sodium chloride, the at least one zwitterionic surfactant is cocamidopropyl betaine, the at least one reducing agent is sucrose and the water is deionized water.

26. The method of claim 25, wherein the composition further comprises a fragrance.

27. The method of claim 26, wherein the composition comprises about 0.90 wt % of sodium chloride, about 2.0 wt % of cocamidopropyl betaine, about 1.0 wt % of benzalkonium chloride, about 2.0 wt % of sucrose, 0.05 wt % of a fragrance.

28. The method of claim 27, wherein the fragrance is orange oil.

* * * * *